United States Patent [19]

Hashimoto et al.

[11] 4,160,822

[45] Jul. 10, 1979

[54] DENTIFRICES

[75] Inventors: Shigeru Hashimoto, Omihachiman; Kenji Inoue, Takatsuki, both of Japan

[73] Assignee: Sunstar Hamigaki Kabushiki Kaisha, Takatsuki, Japan

[21] Appl. No.: 837,101

[22] Filed: Sep. 28, 1977

[30] Foreign Application Priority Data

Oct. 25, 1976 [JP] Japan .................................. 51-129013
Mar. 29, 1977 [JP] Japan .................................. 52-35998

[51] Int. Cl.² .............................................. A61K 7/18
[52] U.S. Cl. ..................................................... 424/52
[58] Field of Search ........................................... 424/52

[56] References Cited

U.S. PATENT DOCUMENTS 3,941,877  3/1976  King et al. ............................. 424/52
3,966,901  6/1976  Cullum et al. ......................... 424/52

OTHER PUBLICATIONS

Osipow, L., Marra, D., and Snell, F. D., "Cosmetics Containing Sucrose Esters", Drug and Cosmetic Industry, Mar. 1957, pp. 312–313, 396–397.

*Primary Examiner*—Natalie Trousof
*Assistant Examiner*—Robert C. Whittenbaugh
*Attorney, Agent, or Firm*—Stevens, Davis, Miller & Mosher

[57] ABSTRACT

A dentifrice comprising an improved foaming agent in admixture with other conventional ingredients for dentifrice, such as a polishing agent, a thickening agent and a wetting agent, which is characterized in that the improved foaming agent comprises a sucrose fatty acid ester, an N-acylamino acid or a salt thereof and sodium monofluorophosphate.

16 Claims, No Drawings

DENTIFRICES

The present invention relates to dentifrices, more particularly, to dentifrices containing a sucrose fatty acid ester as a foaming agent having a lower toxicity, which have improved foaming properties, exhibit more efficacious prevention against tooth decay and do not change a taste of food after brushing teeth with them.

Dentifrices are usually incorporated with a surfactant as a foaming agent in admixture with other ingredients, such as a polishing agent, a thickening agent and a wetting agent in order to provide detergency, dispersion-emulsion properties, foaming properties or the like. It is considered that a surfactant used as a foaming agent is an essential ingredient of a dentifrice since, when brushing teeth, a surfactant lowers surface tention of the dentifrice to improve detergency thereof, accelerates dispersion and penetration of a pharmacologically active ingredient contained in the dentifrice to enhance the efficacy thereof and foams in the mouth to satisfy a feeling of brushing teeth.

The surfactant used as a foaming agent should have not only good properties but lowering a surface tension, foaming or the like, but also good properties with respect to taste, odor or the like since it is mouthed. Thus, it has been employed an anionic surfactant such as sodium alkylsulfate, sodium acylsarcosine, α-olefin sulfonate, sodium coconut monoglyceride sulfate or the like. Among these surfactants, sodium alkylsulfate is most commonly used since it has good properties. However, sodium alkylsulfate has a serious defect of changing a taste of food after brushing teeth with a dentifrice containing it, which may be caused by adsorption of the surfactant to a taste bud and oral mucosa. Furthermore, sodium alkylsulfate somewhat irritates oral mucosa and inactivates an enzyme added to a dentifrice as a pharmacologically active ingredient. It is said that an α-olefin sulfonate and sodium acylsarcosine have a good taste and hardly change a taste of food after brushing teeth with a dentifrice containing them. However, the α-olefin sulfonate has a problem in respect of toxicity. Although sodium acylsarcosine has no problem in respect of toxicity since it is decomposed into a fatty acid and an amino acid (sarcosine) in the living body, it induces undesirable peeling of oral mucosa when used in a large amount (i.e. more than 0.5% by weight on the basis of total weight of a dentifrice) and provides, on the other hand, poor foaming properties when used in a small amount.

Under these circumstances, it has been suggested to employ a sucrose fatty acid ester (hereinafter, referred to as "sugar ester") as a lower toxic surfactant in a dentifrice. The sugar ester has a lower toxicity and is one of a few surfactants which are admitted as a food additive. Moreover, the sugar ester does not inactivate an enzyme added to a dentifrice as a pharmacologically active ingredient. However, the sugar ester has some defects, such as poor foaming properties and inferior effect and feeling in brushing teeth. From this standpoint, only a few reports have been published with respect to dentifrices incorporated with a sugar ester, for instance, Osipow, L., Marra, D., and Snell, F. D., "COSMETICS Containing Sucrose Esters", DRUG AND COSMETIC INDUSTRY, March, 1957, wherein a sugar ester such as sucrose monopalmitate is used.

The present inventors have intensively studied on the foaming properties of dentifrices containing a sugar ester, and it has now been found that the foaming properties of the sugar ester can be extremely improved when it is used in combination with an N-acylamino acid or a salt thereof and sodium monofluorophosphate.

An object of the present invention is to provide a dentifrice having improved foaming properties. Another object of the invention is to provide a dentifrice containing a sugar ester, an N-acylamino acid or a salt thereof and sodium monofluorophosphate as a foaming agent in admixture with other conventional ingredients for dentifrices, which has improved foaming properties and good effect and feeling in brushing teeth. These and other objects of the invention will be apparent from the following description.

Sodium monofluorophosphate is well known as an ingredient of a dentifrice. It is also known, to use an N-acylamino acid or a salt thereof in a dentifrice (cf, Japanese Patent Publication Nos. 24480/1970 and 20720/1971). However, it has never been taught or even suggested to use sodium monofluorophosphate and an N-acylamino acid or a salt thereof in order to improve the foaming properties of a dentifrice containing a sugar ester.

According to the present invention, there is provided a dentifrice containing a sugar ester in combination with an N-acylamino acid or a salt thereof and sodium monofluorophosphate as a foaming agent. The dentifrice of the present invention has improved foaming properties and no defect of changing a taste of food after brushing teeth as seen in the conventional dentifrices containing sodium alkylsulfate. Moreover, the dentifrice of the present invention exhibits more efficacious prevention against tooth decay due to addition of sodium monofluorophosphate. Although an N-acylamino acid or a salt thereof other than acylsarcosine salts causes undesirable peeling of oral mucosa in an amount of more than about 0.75% by weight, in case of acylsarcosine salts, in an amount of more than about 0.5% by weight, on the basis of the total weight of a dentifrice, it has further been found that incorporation of a sugar ester is effective for prevention of the peeling of oral mucosa and that the N-acylamino acid including N-acylsarcosine, or a salt thereof can be used up to about 2% by weight without occurrence of the undesirable peeling of oral mucosa.

In the following Table 1, there are shown the test results of foaming properties of dentifrices containing various foaming agents and peeling of oral mucosa when brushing teeth with the dentifrices.

The dentifrices to be tested were prepared in the same manner as described in Example 1 hereinafter, in which the amount of the foaming agents was varied using sodium lauroylsarcosine or sodium N-lauroyl-N-methyl-β-alanine as the N-acylamino acid salt and DK ester F-160 or F-50 (trade marks of sugar esters produced and sold by Daiichi Kogyo Seiyaku K.K. in Japan, monoester contents thereof are 70% and 30%, respectively) as the sugar ester. The foaming properties were shown by the foam height and the feeling of brushing. The foam height (cm) was measured according to Ross-Miles test method by diluting the dentifrice to 1/10 by volume with water and then measuring the foam height after one minute. The feeling of brushing teeth was estimated according to the following criteria:

A: Foaming is enough to give satisfaction in a feeling of brushing.

B: Foaming is acceptable for a dentifrice.
C: Foaming is insufficient.
D: Foaming is hardly observed.

The peeling of oral mucosa was determined by observing oral mucosa of 10 persons, who have sensitive oral micosa, after brushing teeth. The result of peeling of oral mucosa was recorded by the number of the persons who showed peeling of oral mucosa.

Table 1

| Foaming agents (%) | | | | | Foaming Properties | | Peeling of oral mucosa |
|---|---|---|---|---|---|---|---|
| Sugar ester* | | Sodium lauroyl-sarcosine | Sodium N-lauroyl-N-methyl-β-alanine | Sodium monofluorophosphate | Foam height (cm) | Feeling | |
| F-160 | F-50 | | | | | | |
| — | — | 0.5 | — | — | 1.5 – 0 | D | 0 |
| — | — | — | 0.5 | — | 1.7 – 0 | D | 0 |
| 2 | — | — | — | — | 2.0 | D | 0 |
| — | 2 | — | — | — | 1.0 | D | 0 |
| 2 | — | 0.5 | — | — | 3.2 | D | 0 |
| — | 2 | 0.5 | — | — | 2.0 | D | 0 |
| — | 2 | 0.5 | — | 0.15 | 8.9 | C | 0 |
| — | 2 | 0.5 | — | 0.37 | 10.4 | A – B | 0 |
| — | 2 | 0.5 | — | 0.74 | 11.8 | A | 0 |
| — | 2 | 0.5 | — | 1.11 | 13.0 | A | 0 |
| 2 | — | 0.5 | — | 0.74 | 13.0 | A | 0 |
| — | — | 0.5 | — | 0.74 | 2.0 – 0 | D | 0 |
| — | 2 | — | — | 0.74 | 1.0 | D | 0 |
| 2 | — | — | 0.5 | — | 3.0 | D | 0 |
| — | 2 | — | 0.5 | — | 2.0 | D | 0 |
| — | 2 | — | 0.5 | 0.15 | 8.5 | C | 0 |
| — | 2 | — | 0.5 | 0.37 | 10.3 | B – C | 0 |
| — | 2 | — | 0.5 | 0.76 | 11.8 | A | 0 |
| — | 2 | — | 0.5 | 1.11 | 13.0 | A | 0 |
| 2 | — | — | 0.5 | 0.76 | 13.2 | A | 0 |
| — | — | — | 0.5 | 0.76 | 3.5 – 0 | D | 0 |
| — | — | — | 0.75 | 0.76 | 8.0 | D | 6 |
| 2 | — | — | 0.75 | 0.76 | 15.5 | A | 0 |
| — | — | — | 1.0 | 0.76 | 10.0 | B – C | 8 |
| 2 | — | — | 1.0 | 0.76 | 18.0 | A | 2 |
| 2 | — | — | 1.0 | — | 7.0 | C – D | 2 |
| — | 2 | — | 1.0 | — | 5.0 | C – D | 2 |

[Note]:
*DK ester

As shown in Table 1, when the sugar ester is used alone, the foaming properties and feeling of brushing teeth with the dentifrice are inferior and are not improved by adding thereto either one of sodium lauroyl-sarcosine, sodium N-lauroyl-N-methyl-β-alanine or sodium monofluorophosphate. On the other hand, when the sugar ester is used in combination with the N-acylamino acid and sodium monofluorophosphate, the foaming properties and peeling of brushing teeth with the dentifrice are remarkably improved. The foam height is a little different by varying the kind of the sugar ester, but the feeling of brushing is not affected by the variation of sugar ester. Although N-lauroyl-N-methyl-β-alanine induces peeling of oral mucosa in an amount of 0.75% by weight. The peeling of oral mucosa can be inhibited by incorporating the sugar ester. The dentifrice containing only 1.00% of N-lauroyl-N-methyl-β-alanine and 0.74% of sodium monofluorophosphate as the foaming agent has relatively improved foaming properties, but it has still a defect that it induces peeling of oral mucosa. Other N-acylamino acids and salts thereof show similar results.

The sugar ester used in the present invention may be any commercially available sugar ester, for example, DK ester F-50, F-70, F-90, F-110, F-140 or F-160 (sugar esters produced and sold by Daiichi Kogyo Seiyaku K.K., containing fatty acid residues derived from hardened tallow and 30, 40, 50, 60 and 70% of monoester, respectively) or DK ester L-18 (sucrose monolaurate produced and sold by Daiichi Kogyo Seiyaku K.K.). These sugar esters are an ester of sucrose with a fatty acid. Carbon number of the fatty acids is not critical, but the fatty acids have usually 8 to 20 carbon atoms, preferably 12 to 18 carbon atoms. Suitable examples of the fatty acids are saturated fatty acids (e.g. lauric acid, myristic acid, palmitic acid, stearic acid, etc.) and unsaturated fatty acids (e.g. oleic acid, elaidic acid, linolic acid, linolenic acid, arachidonic acid, erucic acid, etc.). The degree of esterification is not critical, either, and mono-ester to tri-ester are included. The commercially available sugar esters are usually a mixture of various esters of sucrose with one or more fatty acids having various degrees of esterification, but usually a mixture of mono-, di- and tri-esters whereing at least 10% by weight of a mono ester is contained. The sugar ester is used in an appropriate amount, and is preferably in the range of from 0.25 to 10% by weight, more preferably 0.25 to 5% by weight, based on the total weight of the dentifrice.

Generally, sugar esters are prepared by reacting sucrose with fatty acid(s) in the presence of sodium salt of the fatty acid and it is difficult to avoid the contamination of the unreacted fatty acid and sodium salt thereof. For instance, sugar esters are permitted to contain the unreacted fatty acid derivatives corresponding to not more than 5.0% of acid value and not more than 1.5% of residue on ignition in Food Additives Formulary. Commercially available sugar esters contain usually 5 to 9% by weight of the unreaced fatty acid derivatives.

We have further found that the foaming properties and the storage stability of the dentifrice are affected by the unreacted fatty acid derivatives in the sugar ester and that these defects are eliminated by using a sugar ester containing not more than 4% by weight of the unreacted fatty acid derivatives. Furthermore, although sugar esters are usually incorporated into the dentifrice after dissolving in a solvent such as glycerin by heating a dispersion thereof in the solvent at about 60° C., when the sugar ester containing not more than 4% by weight of the unreacted fatty acid derivatives is used, this heating step can be ommited. Therefore, in the present invention, it is preferably to use the sugar ester containing not more than 4% by weight of the unreacted fatty acid derivatives.

To obtain the sugar ester containing not more than 4% by weight of the unreacted fatty acid derivatives, a crude product prepared by reacting sucrose with fatty acid(s) in the presence of sodium salt thereof is washed with a solvent such as aqueous acetone or aqueous ethanol.

In the following Table 2, there are shown the test results of the relation between the content of the unreacted fatty acid derivatives in the sugar ester (30% of monoester content) and the foaming properties and the storage stability of the dentifrice.

The test was carried out by preparing samples of dentifrices according to the formula shown in Example 2 hereinafter by two processes. In one process (A), the sugar ester was mixed with other ingredients in a solution prepared by dispersing in glycerin and heated at 60° C. In the other process (B), the sugar ester was mixed with the other ingredients in a powdered form. The foaming properties were determined by the same eprocedure in the above Table 1.

an N-lower alkyl ($C_1$ to $C_4$) substituent, and the acyl group is a fatty acid residue having 8 to 22 carbon atoms, preferably, lauroyl, myristoyl, stearyl, oleoyl or linoleoyl; and a salt thereof with alkali metal such as sodium or potassium. As described above, the N-acylamino acid or its salt causes peeling of oral mucosa in an amount of more than 0.75% by weight in case of N-acylamino acids or their salts other than N-acylsarcosine or its salt, and in an amount of more than 0.5% by weight in case of N-acylsarcosine or its salt. However, in the present invention, the N-acylamino acid or their salts including N-acylsarcosine or its salt can be used in an amount up to 2% by weight based on the total weight of the dentifrice. When a larger amount of the N-acylamino acid or its salt is used, a larger amount of the sugar ester is needed. Preferred amount of the N-acylamino acid or its salt is 0.1 to 1% by weight, more preferably, 0.1 to 0.75% by weight based on the total weight of the dentifrice. When N-acylsarcosine or its salt is used, 0.1 to 0.5% by weight based on the total weight of the dentifrice is preferable.

Sodium monofluorophosphate is usually added to the dentifrice of the present invention in an amount of not more than 1.1%, preferably 0.15 to 1.1%, more preferably, 0.15 to 0.76% by weight based on the total weight of the dentifrice (fluorine content: 200 to 1,000 ppm) since physical properties of the dentifrice is lowered when a larger amount is used.

The dentifrice of the present invention is produced by

Table 2

| Process | Period of storage | Content of the unreacted fatty acid derivatives in the sugar ester (% by weight) | | | | | | | | | | | |
|---|---|---|---|---|---|---|---|---|---|---|---|---|
| | | 2 | | 4 | | 5 | | 6 | | 7 | | 8 | |
| | | Foam height (cm) | Feeling | Foam height (cm) | Feeling | Foam height (cm) | Feeling | Foam height (cm) | Feeling | Foam height (cm) | Feeling | Foam height (cm) | Feeling |
| A | right after production | 14.5 | A | 14.0 | A | 13.5 | A | 13.0 | A | 10.0 | B | 6.0 | D |
| | 2 months at 55° C. | 14.5 | A | 14.0 | A | 13.5 | A | 13.0 | A | 7.0 | C | 2.0 | D |
| | 4 months at 40° C. | 14.5 | A | 14.0 | A | 13.5 | A | 13.0 | A | 8.0 | C | 2.0 | D |
| | 2 months at 0° C. | 14.5 | A | 14.0 | A | 7.0 | C | 6.5 | C | 6.0 | C | 2.0 | D |
| B | right after production | 14.5 | A | 14.0 | A | 11.0 | B | 9.0 | C | 7.0 | C | 5.0 | D |
| | 2 months at 55° C. | 14.5 | A | 14.0 | A | 9.0 | C | 8.0 | C | 5.0 | D | 2.0 | D |
| | 4 months at 40° C. | 14.5 | A | 14.0 | A | 9.0 | C | 8.0 | C | 5.0 | D | 2.0 | D |
| | 2 months at 0° C. | 14.5 | A | 14.0 | A | 6.0 | D | 6.0 | D | 5.0 | D | 2.0 | D |

As shown in Table 2, when the content of the unreacted fatty acid derivatives is more than 7%, the foam height is insufficient even right after the production of the dentifrice and considerably lowered in the storage for a long time. When the content of the unreacted fatty acid derivatives is 5 to 6%, the foam height of the dentifrice prepared by Process A is sufficient except that in storage at low temperature for a long time whereas the foam height of the dentifrice prepared by Process B is insufficient. On the other hand, when the content of the unreacted fatty acid derivatives is not more than 4%, the foam height of the dentifrice prepared by either Process A or B is sufficient at any time of the storage.

The N-acylamino acid or its salt used in the present invention includes various N-acylated derivatives of amino acids, wherein the amino acid is, for example, sarcosine, alanine, phenylalanine, leucine, isoleucine, methionine, proline, tryptophane, valine, serine, tyrosine, glutamic acid, ε-aminocaproic acid or those having a conventional technique. When the sugar ester containing not more than 4% by weight of the unreacted fatty acid derivatives is used, it can be mixed with other ingredients in the powdered form as described above.

A wide variety of preparation forms can be employed, for example, the preparation may be in the form of tooth powder, toothpaste, dental cream, tooth wash or the like.

The other ingredients of the dentifrice of the present invention include all conventional ingredients for dentifrices, for instance, a polishing agent such as calcium secondary phosphate (dihydrate or anhydride), calcium carbonate, silicate, insoluble sodium metaphosphate or the like; a thickening agent such as sodium carboxymethylcellulose, carageen, sodium alginate, bentonite, silicic acid anhydride or the like; and a wetting agent such as glycerin, sorbitol, propylene glycol, sodium pyrrolidonecarboxylate, polyethylene glycol or the like.

Moreover, the dentifrice of the present invention may contain a pharmacologically active ingredient such as an allantoin derivative, a salt of glycyrrhizic acid, chlorhexidine, hinokitiol, dextranase, lysozyme, sodium chloride, tranexamic acid, ε-aminocaproic acid or the like.

The following Examples are designed to illustrate the practice of the present invention but not to limit the scope of the invention.

EXAMPLE 1

| Ingredients | % by weight |
| --- | --- |
| Calcium secondary phosphate dihydrate | 45.00 |
| Sodium carboxymethylcellulose | 0.50 |
| Carrageen | 0.50 |
| Glycerin | 10.00 |
| Sorbitol | 10.00 |
| Water | 29.44 |
| Sugar ester (DK ester F-50) | 2.00 |
| Sodium N-lauroyl-N-methyl-β-alanine | 0.50 |
| Flavor | 1.00 |
| Saccharin sodium | 0.20 |
| Preservative | 0.10 |
| Sodium monofluorophosphate | 0.76 |

According to the above formula, a toothpaste is prepared by a conventional technique.

EXAMPLE 2

| Ingredients | % by weight |
| --- | --- |
| Calcium secondary phosphate dihydrate | 45.00 |
| Sodium carboxymethylcellulose | 0.50 |
| Carrageen | 0.50 |
| Glycerin | 10.00 |
| Sorbitol | 10.00 |
| Water | 29.44 |
| Sugar ester (monoester content: 30% by weight, unreacted fatty acid content: 2.0% by weight) | 2.00 |
| Sodium N-lauroylsarcosine | 0.50 |
| Flavor | 1.00 |
| Saccharin sodium | 0.20 |
| Preservative | 0.10 |
| Sodium monofluorophosphate | 0.76 |

According to the above formula, the sugar ester is mixed with calcium secondary phosphate in the powdered form and added thereto the other ingredients to give a toothpaste.

EXAMPLE 3

| Ingredients | % by weight |
| --- | --- |
| Calcium secondary phosphate | 45.00 |
| Sodium carboxymethylcelluloe | 0.50 |
| Carrageen | 0.50 |
| Glycerin | 10.00 |
| Sorbitol | 10.00 |
| Water | 30.44 |
| Sugar ester (monoester content: 50% by weight, unreacted fatty acid content: 3.0% by weight) | 1.00 |
| Sodium N-lauroylsarcosine | 0.50 |
| Flavor | 1.00 |
| Saccharin sodium | 0.20 |
| Preservative | 0.10 |
| Sodium monofluorophosphate | 0.76 |

According to the above formula, a toothpaste is prepared by a conventional technique.

EXAMPLE 4

| Ingredients | % by weight |
| --- | --- |
| Calcium carbonate | 40.00 |
| Sodium carboxymethylcellulose | 0.50 |
| Carrageen | 0.50 |
| Glycerin | 13.00 |
| Sorbitol | 7.00 |
| Silicic acid anhydride | 1.50 |
| Water | 32.94 |
| Sugar ester (DK ester F-160) | 2.00 |
| Sodium N-myristoyl-N-methyl-β-alanine | 0.50 |
| Flavor | 1.00 |
| Saccharin sodium | 0.20 |
| Preservative | 0.10 |
| Sodium monofluorophosphate | 0.76 |

According to the above formula, a toothpaste is prepared by a conventional technique.

EXAMPLE 5

| Ingredients | % by weight |
| --- | --- |
| Calcium carbonate | 40.00 |
| Sodium carboxymethylcellulose | 0.50 |
| Carrageen | 0.50 |
| Glycerin | 13.00 |
| Sorbitol | 7.00 |
| Silicic acid anhydride | 1.50 |
| Water | 32.94 |
| Sugar ester (DK ester F-50) | 2.00 |
| Sodium lauroylsarcosine | 0.50 |
| Flavor | 1.00 |
| Saccharin sodium | 0.20 |
| Preservative | 0.10 |
| Sodium monofluorophosphate | 0.76 |

According to the above formula, a toothpaste is prepared by a conventional technique.

"Orange Juice Effect" (a phenomenon of taste change when one has a sour food, especially, orange juice after brushing teeth, see Japanese Patent Publication No. 43830/1972) was tested using the toothpaste of Example 1. Five panel members drank a glass of orange juice after brushing teeth with the toothpaste and estimated the taste according to the following criteria:
0: No taste change
1: Scarcely taste change
2: A little taste change
3: Taste change
4: Considerably taste change As a control, a toothpaste was prepared according to Example 1 in which 2% by weight of sodium laurylsulfate was substituted for the sugar ester and sodium N-lauroyl-N-methyl-β-alanine. The results are shown in the following Table 3.

Table 3

| Panel member | Toothpaste of Example 1 | Control |
| --- | --- | --- |
| A | 0 | 3 |
| B | 1 | 4 |
| C | 0 | 3 |
| D | 0 | 3 |
| E | 0 | 4 |
| Average | 0.2 | 3.4 |

As shown in Table 3, the toothpaste of the present invention hardly changes a taste of food after brushing teeth with it.

What is claimed is:

1. A dentifrice comprising a foaming agent in admixture with other conventional ingredients for dentifrice, said foaming agent comprising a sucrose fatty acid ester, an N-acylamino acid or a salt thereof and sodium monofluorophosphate.

2. The dentifrice according to claim 1, wherein the sucrose fatty acid ester is a mixture of mono-, di- and tri-ester of sucrose with at least one fatty acid having 8 to 20 carbon atoms which contains at least 10% by weight of a mono-ester.

3. The dentifrice according to claim 2, wherein the sucrose fatty acid ester contains not more than 4% by weight of unreacted fatty acids.

4. The dentifrice according to claim 1, wherein the sucrose fatty acid ester is contained in an amount of 0.25 to 10% by weight based on the total weight of the dentifrice.

5. The dentifrice according to claim 4, wherein the content of the sucrose fatty acid ester is in the range of 0.25 to 5% by weight based on the total weight of the dentifrice.

6. The dentifrice according to claim 1, wherein the acyl group of the N-acylamino acid or a salt thereof is an fatty acid residue having 8 to 22 carbon atoms.

7. The dentifrice according to claim 6, wherein the N-acylamino acid or a salt thereof is contained in an amount up to 2% by weight based on the total weight of the dentifrice.

8. The dentifrice according to claim 7, wherein the N-acylamino acid or a salt thereof is contained in an amount of 0.1 to 0.75% by weight based on the total weight of the dentifrice.

9. The dentifrice according to claim 8, wherein the N-acylamino acid or a salt is N-lauroyl-N-methyl-$\beta$-alanine or its sodium salt.

10. The dentifrice according to claim 8, wherein the N-acylamino acid or a salt is N-myristoyl-N-methyl-$\beta$-alanine or its sodium salt.

11. The dentifrice according to claim 8, wherein the N-acylamino acid or a salt is N-lauroyl-sarcosine or its sodium salt.

12. The dentifrice according to claim 11, wherein N-lauroylsarcosine or its sodium salt is contained in an amount of 0.1 to 0.5% by weight based on the total weight of the dentifrice.

13. The dentifrice according to claim 1, wherein sodium monofluorophosphate is contained in an amount of not more than 1.1% by weight based on the total weight of the dentifrice.

14. The dentifrice according to claim 13, wherein the content of sodium monofluorophosphate is in the range of 0.15 to 0.76% by weight based on the total weight of the dentifrice.

15. A method of improving the foaming characteristics of a dentifrice comprising mixing a foaming agent therein consisting essentially of a sucrose fatty acid ester, an N-acylamino acid or a salt thereof and sodium monofluorophosphate.

16. In a dentifrice composition, a foaming agent consisting essentially of a sucrose fatty acid ester, an N-acylamino acid or a salt thereof and sodium monofluorophosphate.

* * * * *